(12) United States Patent
Freiding

(10) Patent No.: US 10,973,677 B2
(45) Date of Patent: *Apr. 13, 2021

(54) COMFORT LAYER FOR A COLLECTING BAG

(71) Applicant: Coloplast A/S, Humlebaek (DK)

(72) Inventor: Markus Freiding, Helsingborg (SE)

(73) Assignee: Coloplast A/S, Humlebaek (DK)

( * ) Notice: Subject to any disclaimer, the term of this patent is extended or adjusted under 35 U.S.C. 154(b) by 217 days.

This patent is subject to a terminal disclaimer.

(21) Appl. No.: 16/005,708

(22) Filed: Jun. 12, 2018

(65) Prior Publication Data

US 2018/0289528 A1 Oct. 11, 2018

Related U.S. Application Data

(63) Continuation of application No. 14/402,692, filed as application No. PCT/DK2013/050150 on May 17, 2013, now Pat. No. 10,045,878.

(30) Foreign Application Priority Data

May 25, 2012 (DK) .......................... PA 2012 70279

(51) Int. Cl.
| | | |
|---|---|---|
| *A61F 5/445* | (2006.01) | |
| *A61F 5/44* | (2006.01) | |
| *B31B 70/00* | (2017.01) | |
| *B31B 70/64* | (2017.01) | |

(52) U.S. Cl.
CPC ............ *A61F 5/445* (2013.01); *A61F 5/4404* (2013.01); *B31B 70/00* (2017.08); *B31B 70/64* (2017.08); *B31B 2241/00* (2013.01)

(58) Field of Classification Search
CPC combination set(s) only.
See application file for complete search history.

(56) References Cited

U.S. PATENT DOCUMENTS

| | | | |
|---|---|---|---|
| 4,439,191 A | | 3/1984 | Hogan |
| 4,728,323 A | * | 3/1988 | Matson .................. A61L 15/46 |
| | | | 604/304 |
| 5,403,299 A | | 4/1995 | Schneider |
| (Continued) | | | |

FOREIGN PATENT DOCUMENTS

| | | |
|---|---|---|
| CN | 1511016 A | 7/2004 |
| CN | 102065803 A | 5/2011 |
| (Continued) | | |

OTHER PUBLICATIONS

EPO Communication of Notice of Opposition received for European Patent Application No. 13728310.7, dated May 7, 2018, 1 page.

(Continued)

*Primary Examiner* — Guy K Townsend
(74) *Attorney, Agent, or Firm* — Coloplast Corp.; Nick Baumann

(57) ABSTRACT

A collecting bag for human body wastes having a barrier film covered by a comfort layer attached to the barrier film in an attachment zone wherein the comfort layer is a textile material that is attached to said barrier film in one or more zones of attachment and wherein threads of the textile material have a higher melting point than that of the barrier film material in the attachment zone.

19 Claims, 2 Drawing Sheets

(56) References Cited

U.S. PATENT DOCUMENTS

| | | | |
|---|---|---|---|
| 5,759,180 A * | 6/1998 | Myhres | A61F 5/445 428/343 |
| 5,800,928 A | 9/1998 | Fischer et al. | |
| 6,135,986 A * | 10/2000 | Leisner | A61F 5/441 604/322 |
| 6,246,835 B1 | 6/2001 | Manabe | |
| 6,709,421 B1 * | 3/2004 | Falconer | A61F 5/445 604/335 |
| 7,160,275 B2 * | 1/2007 | Falconer | A61F 5/441 604/333 |
| 7,214,217 B2 * | 5/2007 | Pedersen | A61F 5/441 604/332 |
| 7,517,339 B2 * | 4/2009 | Pedersen | A61F 5/448 604/345 |
| 7,604,622 B2 * | 10/2009 | Pedersen | A61F 5/448 604/333 |
| 7,931,631 B2 * | 4/2011 | Pedersen | B32B 1/02 604/344 |
| 8,118,797 B2 * | 2/2012 | Giori | A61L 28/0069 604/332 |
| 9,050,387 B2 | 6/2015 | Chang et al. | |
| 10,045,878 B2 * | 8/2018 | Freiding | B31B 70/00 |
| 2002/0064614 A1 | 5/2002 | Turnbull | |
| 2004/0049837 A1 | 3/2004 | Falconer et al. | |
| 2004/0147887 A1 * | 7/2004 | Hagstroem | A61F 5/445 604/332 |
| 2004/0204694 A1 * | 10/2004 | Nicholson | A61F 2/0063 604/327 |
| 2005/0015065 A1 * | 1/2005 | Falconer | A61F 5/445 604/335 |
| 2005/0084634 A1 | 4/2005 | Giori | |
| 2005/0113770 A1 * | 5/2005 | Pedersen | B32B 1/02 604/332 |
| 2005/0143696 A1 * | 6/2005 | Pedersen | A61F 5/441 604/332 |
| 2005/0159717 A1 | 7/2005 | Holtermann | |
| 2005/0273064 A1 * | 12/2005 | Dircks | B32B 7/12 604/322 |
| 2007/0027434 A1 * | 2/2007 | Pedersen | A61F 5/448 604/333 |
| 2007/0203466 A1 * | 8/2007 | Pedersen | A61F 5/441 604/333 |
| 2008/0033379 A1 | 2/2008 | Pedersen | |
| 2008/0119773 A1 * | 5/2008 | Flick | A61F 13/00008 602/48 |
| 2008/0294129 A1 * | 11/2008 | Giori | A61L 28/0057 604/332 |
| 2009/0143755 A1 | 6/2009 | Schertiger | |
| 2009/0163885 A1 * | 6/2009 | Pedersen | A61F 5/448 604/333 |
| 2010/0322989 A1 | 12/2010 | Martin | |
| 2011/0289923 A1 * | 12/2011 | Bittner | F22B 37/008 60/670 |
| 2014/0371698 A1 | 12/2014 | Chang et al. | |
| 2015/0133881 A1 * | 5/2015 | Freiding | B31B 70/00 604/339 |
| 2015/0265454 A1 * | 9/2015 | Oeelund | A61F 5/44 604/344 |
| 2018/0289528 A1 * | 10/2018 | Freiding | B31B 70/00 |

FOREIGN PATENT DOCUMENTS

| | | |
|---|---|---|
| EP | 0443728 A2 | 8/1991 |
| EP | 0985390 A1 | 3/2000 |
| EP | 1389081 A1 | 2/2004 |
| EP | 2108345 A1 | 10/2009 |
| EP | 2289471 A1 | 3/2011 |
| EP | 2854723 A1 | 4/2015 |
| FR | 3008880 A1 | 1/2015 |
| GB | 2064333 A | 6/1981 |
| GB | 2216007 A | 10/1989 |
| GB | 2239838 A | 7/1991 |
| GB | 2287193 A | 9/1995 |
| GB | 2473206 A | 3/2011 |
| JP | 4128724 U | 11/1992 |
| JP | 2540842 Y | 7/1997 |
| JP | 2000111987 A | 4/2000 |
| JP | 2004524944 A | 8/2004 |
| JP | 2007-508906 A | 4/2007 |
| JP | 2008-501554 | 1/2008 |
| JP | 2010111987 A | 5/2010 |
| JP | 2011514328 A | 5/2011 |
| RU | 2220685 C1 | 1/2004 |
| WO | 20021094143 A1 | 11/2002 |
| WO | 20021102289 A1 | 12/2002 |
| WO | 20031020188 A1 | 3/2003 |
| WO | 20031022186 A1 | 3/2003 |
| WO | 20041069113 A1 | 8/2004 |
| WO | 20051041827 A2 | 5/2005 |
| WO | 20051120827 A1 | 12/2005 |
| WO | 20061026995 A1 | 3/2006 |
| WO | 20081074333 A1 | 6/2008 |
| WO | 20081112337 A1 | 9/2008 |
| WO | 10041766 A1 | 4/2010 |
| WO | 20101077377 A1 | 7/2010 |
| WO | 20131174382 A1 | 11/2013 |

OTHER PUBLICATIONS

Coloplast's Response to Notice of Opposition received May 7, 2018 for European Patent Application No. 13728310.7, dated Sep. 14, 2018, 10 pages.

Coloplast Inc., "The Coloplast (Registered) mc2002 Ostomy System. The gentle and flexible two-piece generation" Coloplast Inc., Aug. 6, 1984, 2 pages.

Collection of documents relating to a 510K submission to the Food and Drug Administration, released/published in response to a freedom of information request, May 8, 1985, cited in opposition by Hollister Inc., in European Patent Application No. 17173921.2, Notice of Opposition dated Jun. 4, 2020, 85 pages.

Hollister Inc. internal form to describe and catalogue competitor products, Jun. 25, 1985, cited in opposition by Hollister Inc., in European Patent Application No. 17173921.2, Notice of Opposition dated Jun. 4, 2020, 1 page.

Hollister Inc. internal form to describe and catalogue competitor products, Feb. 10, 1984, cited in opposition filed by Hollister Inc., in European Patent Application No. 17173921.2, Notice of Opposition dated Jun. 4, 2020, 21 pages.

Advertisement for Coloplast mc2000 and mc2002 Ostomy System, Journal of Enterostomal Therapy, May/Jun. 1984, 3 pages.

Advertisement for Coloplast, "The Gentle and Flexible Generation, mc2000, mc2002 and URO2002", Nursing Times, May 30-Jun. 5, 1984, 3 pages.

Coloplast brochure distributed in the United Kingdom describing the COLOPLAST mc2000 (1-piece) and mc2002 (2-piece) ostomy systems and the uro2002 system, 14 pages.

EPO Communication of a notice of opposition received for European Patent Application No. 17173921.2, dated Jun. 4, 2020, 36 pages.

EPO Communication of a Notice of Opposition and Opposition filed by Hollister Inc. in European Patent Application No. 17173921. 2/patent No. 325467, dated Jun. 4, 2020, 184 pages.

EPO Communication of a Notice of Opposition and Opposition filed by Salts Healthcare Ltd. in European Patent Application No. 17173921.2/patent No. 325467, dated Jun. 5, 2020, 106 pages.

EPO Decision revoking the European Patent received for European Patent Application No. 13728310.7, dated Nov. 18, 2019, 25 pages.

Coloplast Inc. Brochure, "The Coloplast choice of two gentle, flexible ostomy systems" Coloplast Inc., 1984, 8 pages.

Coloplast's Notice of appeal filed for European Patent Application No. 13728310.7, dated Jan. 27, 2020, 1 page.

Grounds of opposition filed by Opponent Hollister Inc. in European Patent Application No. 17173921.2/patent 325467, mailed to European Patent Office dated May 22, 2020, 24 pages.

(56) References Cited

OTHER PUBLICATIONS

Communication of a Notice of Opposition with a Request for Documents Pursuant Rule 83 EPC/ Request for translation pursuant Rule 3(3) EPC for EP Patent Application 1713921.2, dated Jun. 4 and Jun. 5, 2020, 2 pages.

EPO Communication of Notice of Oppositions filed by Hollister Inc. and Salts Healthcare Ltd. in European Patent Application No. 17173921.2, dated Jun. 18, 2020, 1 page.

EPO Brief Communication containing Letter from Opponent in reply to the Request for Documents Pursuant Rule 83 EPC/Request for translation pursuant Rule 3(3) received for European Patent Application No. 17173921.2, dated Jun. 25, 2020, 2 pages.

Photograph of Coloplast mc2002 comfort layer side, cited in opposition filed by Hollister Inc., in European Patent Application No. 17173921.2, Notice of Opposition dated Jun. 4, 2020, 1 page.

Photograph of Coloplast mc2002 film layer side, cited in opposition filed by Hollister Inc., in European Patent Application No. 17173921.2, Notice of Opposition dated Jun. 4, 2020, 1 page.

Photographs of Coloplast mc2002 packaging, cited in opposition filed by Hollister Inc., in European Patent Application No. 17173921.2, Notice of Opposition dated Jun. 4, 2020, 2 pages.

International Preliminary Report on Patentability received for PCT Patent Application No. PCT/DK2013/050150, dated Dec. 4, 2014, 8 pages.

International Search Report and Written Opinion received for PCT Patent Application No. PCT/DK2013/050150, dated Jul. 25, 2013, 12 pages.

ASTM Designation: D39391D3939M-11 "Standard Test Method for Snagging Resistance of Fabrics (Mace)", ASTM Int'l, Jan. 30, 2015, 8 pages.

Dansk standard, DS/EN 1049-2, "Textiles—Woven Fabrics—Construction—Methods of Analysis—Part 2: Determination of number of threads per unit length" Jul. 11, 1994, 12 pages.

Dansk standard, DS/EN 12127, "Textiles—Fabrics—Determination of mass per unit area using small samples", Feb. 11, 1998, 10 pages.

Dansk standard, DS/EN ISO 12945-2, "Textiles—Determination of fabric propensity to surface fuzzing and to pilling—Part 2: Modified Martindale method", Nov. 6, 2000, 26 pages.

International Organization for Standardization, ISO 7211/5, "Textiles—Woven fabrics—Construction—Methods of analysis—Part 5: Determination of linear density of yarn removed from fabric", Mar. 15, 1984, 8 pages.

Dansk standard, DS/EN ISO 2060, Textiles—Yarn from packages—Determination of linear density (mass per unit length) by the skein method, Jul. 1, 1997, 22 pages.

\* cited by examiner

COMFORT LAYER FOR A COLLECTING BAG

The invention relates to collecting bags for human body wastes. In particular, the invention relates to a textile comfort layer of a collecting bag providing the collecting bag with an increased resistance against tearing and pulling forces.

BACKGROUND

Collecting bags for receiving and controlling human body wastes are well known and have been provided in numerous shapes, sizes and constructions for many years. Also, collecting bags being provided with a comfort layer to increase user comfort have been provided. Some examples are found in patent publications EP1389081 and U.S. Pat. No. 5,759,180.

In most available collecting bag products in the field of ostomy care, i.e. for bags being part of an ostomy device, such a comfort layer comprises a non-woven material typically made from polyethylene, polypropylene or polyester fibres. The non-woven material is typically heat laminated onto the barrier material of the collecting bag or attached by a welding process. The welding process causes the fibre structure of the non-woven material to melt, and experience shows that this results in a relatively hard or non-flexible welding zone. The resulting attachment or connection between the non-woven and the barrier film layer is relatively strong, i.e. the strength required to peel the two layers apart in a peel strength test is relatively high, but in some cases the materials break instead of being peeled apart, if submitted to such a test. However, the strength of the individual non-woven fibres is compromised or greatly reduced in the melted areas of the material thereby leaving those areas more exposed to failure caused by external forces working on the collecting bag, such as tearing or pulling forces. Indeed, the fact that the welding zone is relatively hard leaves the welding zone area exposed and much more sensitive to notches being created. In the worst case, such a failure may result in the collecting bag being torn up and open and consequently leaking its contents. Furthermore, the process of welding the non-woven onto the barrier material leaves the zone or area of the welding quite visible because all material in the welding zone is mixed and results in a relatively uniform surface after cooling, thus compromising the visual appearance of the collecting bag.

Thus, there is a need for an improved collecting bag that overcomes the above mentioned disadvantages and provides an increased security against failure caused by external forces.

SUMMARY OF THE INVENTION

Therefore, the invention relates to a collecting bag having a textile comfort layer having at least on par peel strength characteristics with traditional non-woven material based comfort layers, but a significantly higher resistance to external forces compared to these. In addition thereto, a collecting bag for human body waste having improved visual and tactile characteristics in the attachment zone(s) between the barrier film material and the comfort layer is achieved. Furthermore, the textile comfort layer has increased resistance to common wear issues such as snagging and pilling.

DETAILED DESCRIPTION OF THE INVENTION

In a first aspect, the invention relates to a collecting bag for human body waste comprising a barrier film covered by a comfort layer, wherein the comfort layer is a textile material having a number of threads each comprising a plurality of fibre filaments, and said textile material is attached to said barrier film in one or more zones of attachment such that not all of the fibre filaments of the textile material in said zone(s) are embedded in the barrier film material.

A textile may be described as a flexible woven material comprising a structured network of threads consisting of fibre filaments. More specifically, the word textile refers to a material made of threads interlacing in a structured way.

In the interlaced structure of a textile the fibre filaments are anchored by the nature of the structure itself compared to the fibres in a non-woven material that are by definition randomly arranged. This explains why a textile material typically has greater strength than non-woven materials.

According to the invention, the textile comfort layer is attached to the barrier film by a heat lamination process or preferably by a welding process. As the textile has a higher melting point than the barrier film, the barrier film material (see detailed description for further detailed features of the barrier film material) will start melting at a relatively low temperature compared to the melting point temperature of the textile material, while the textile does therefore not melt and upholds and remains in its interlaced structure. This also means that the structure of the textile is maintained once the materials have cooled off. In other words, when heat is applied to weld the textile to the barrier film material, the textile does not melt, but the barrier film material melts by the heat applied. The melted barrier film material at least partly flows into the interlaced fibre filament structure of the threads of the textile and thereby creates a physical anchorage between the two layers without destroying the structure of the textile material. Thereby, the textile and the barrier film materials are attached to each other while maintaining the strength of the textile material in the resulting construction. As each thread of the textile material comprises a number of individual fibre filaments, a large resulting surface is provided for the engagement with the melted barrier film material. This has the effect that the peel strength, i.e. the strength required for separating the comfort layer from the barrier film material layer, is relatively high and on par with the peel strength for separating a comfort layer of a non-woven material from a barrier film.

According to embodiments, the peel strength for separating the textile material based comfort layer from the barrier film material is above 5 N/12.5 mm width, such as above 6 N/12.5 mm width or such as above 7 N/12.5 mm width in the zone(s) of attachment. A comparative test is described in the experimental part of the application to support this.

Furthermore, according to the invention, the collecting bag has the additional advantage that an increased resistance against tearing and pulling forces compared to known collecting bags with comfort layers based on non-woven materials is achieved. Particularly, one way of describing this is to show that the collecting bag according to the invention has improved notch sensitivity. Tests have been carried out showing results supporting this finding and the results and methods of these are also presented in the experimental part of the detailed description.

Even further, when the textile comfort layer of the invention is welded onto the barrier film a much less visible and indeed softer welding zone or area is achieved than compared to collecting bags with non-woven comfort layers welded onto the barrier film.

In this application, the term "welding zone" means an area of the comfort layer-barrier film construction where the materials have inter-engaged caused by the welding or heat lamination process. The term "softer" means that the resulting attachment or welding zone is less rigid, or more flexible, when using a textile material according to the invention, than if a non-woven material is used. This is due to the fact that the interlaced structure of the textile is maintained after the welding process, as previously described, and because some, but not all, of the fibre filaments of the threads are wholly or partially embedded in the melted barrier film material. This is fundamentally different from using a non-woven material where practically all of the non-woven and barrier film material in the welding zone melts into a continuous mass which is more hard or rigid once cooled off. Using a textile comfort layer according to the invention, thus also has the consequence that the attachment zone (welding zone) or area has a substantially unchanged visual appearance after the welding process. In other words, when using the textile material, the welded and not-welded surface of the comfort layer looks the same. The physical structure, and thus the feel or tactility of the welded zone or area, is softer than is the case with the welding zone of non-woven material, partly because the textile material stays intact and only bonds with the barrier film instead of melting into a continuous mass, and partly because not all of the fibre filaments are embedded in the melted barrier film material.

In embodiments, those fibre filaments that are not embedded in the barrier film material provide a surface of the comfort layer having the same tactile characteristics as the surface of the comfort layer outside the zone(s) of attachment.

In embodiments, those fibre filaments that are not embedded in the barrier film material provide a surface of the comfort layer having the same visual characteristics as the surface of the comfort layer outside the zone(s) of attachment.

Moreover, in regard to the use of a textile for a collecting bag for human body wastes, a comfort layer made of a textile material provides an increased wear strength compared to the traditionally used non-woven materials in terms of improved resistance against snagging (reference is made to ASTM D3939-11 for test method) and pilling (reference is made to DS/EN ISO 12945-2:2000 for test method).

In short, snagging (also known as a "run" in certain fine textiles such as pantyhose) occurs when a sharp or rough object pulls or drags a group of fibre filaments or a yarn segment from its normal position. Pilling is another surface defect, caused by wear (e.g. washing and daily wearing) and resulting in small balls of fibres forming on the material surface. The textile material based comfort layer according to the invention advantageously has improved resistance to these defects due to the interlaced structure of the material.

This improvement is of particular interest in connection with drainable collecting bags. Drainable bags are often worn and used on the skin surface for a longer period of time than other types of collecting bags and are emptied on a frequent basis. The process of emptying the drainable collecting bag of its contents exposes the bag to friction and tension, particularly because the user often use his/her hands to squeeze or press the collecting bag over a large part of its surface to make sure it is fully emptied. Furthermore, the bag is exposed to repeated friction against the skin and the clothes of the user during normal wear, which increases the likelihood of snagging and pilling of the comfort layer surface. Therefore, when using a textile material according to the present invention, a more wear resistant collecting bag is achieved thereby reducing the risk of untimely product changes thereby adding to increased comfort for the user.

In examples, the collecting bag comprises a first and a second barrier film sealingly joined along at least a part of their edges.

The collecting bag may comprise two identical barrier film blanks being joined along all or part of their edges when the edges are placed on each other. By sealingly joined is to be understood that when the barrier films are joined they form a volume of a collecting bag from which collected output, moisture and bad odour cannot unintendedly escape. The edges of the barrier film blanks may only be joined to each other along a part thereof, particularly in the case of a drainable collecting bag. In such examples, the edges of the barrier film blanks may be in connection with an outlet construction such as, but not limited to, valves and foldable outlet portions.

In examples, the collecting bag further comprises an inlet opening in said barrier film.

The collecting bag may have an inlet opening situated in said barrier film. In the case of a collecting bag comprising a first and a second barrier film, one of the barrier film blanks may typically include the inlet opening. The inlet opening is for allowing the human body wastes to enter into the volume of the collecting bag. The inlet opening of the collecting bag may be placed closer to an upper edge than to a lower edge of the collecting bag as regarded when a user is wearing the collecting bag and is standing up.

In examples, the comfort layer covers the barrier film facing the skin of the user.

The part of the barrier film facing the skin of the user may be covered substantially wholly or only partly by the comfort layer. The comfort layer ensures that the collecting bag does not cling or stick to the skin surface, thereby avoiding a number of unwanted effects as described in the background section. Depending on the type and size of the collecting bag, the comfort layer may only be necessary or desired on part of the barrier film surface. In the case of a collecting bag comprising a first and a second barrier film, the comfort layer may be provided on one or both of the barrier films, i.e. on both sides of the collecting bag, one side facing the user and one side facing away from the user. In some examples, only a certain area percentage of the respective side or sides of the barrier film is covered by the comfort layer. Such area percentage may be 50-95%, such as 60-95%, such as 75-95%, such as approximately 90-95% of the barrier film's surface area.

In examples, the collecting bag is an ostomy bag. The ostomy bag may be permanently attached or connected to one side of an ostomy base plate having a skin-friendly adhesive on the other side thereof for attachment to the skin of a user around a stoma. The base plate has a through-going hole the centre axis of which may be aligned with the centre axis of the inlet opening of the ostomy bag. Alternatively, the ostomy bag may comprise first coupling means for engagement with second mating coupling means on an ostomy base plate.

In examples, the collecting bag is a urine collecting bag. This may include collecting bags used for continence care products, such as separate urine collecting bags having an inlet opening being connectable with one end of a urinary catheter, the other end being inserted into a user's urinary channel. The urine collecting bag could also be of the type being permanently attached or connected to a catheter, in the form of a set-type product solution. In some examples, the collecting bag is a urine collecting leg bag. By mounting the urine collecting bag of the leg of a user one important aspect is that discretion is improved when moving the collecting bag away from the stomach section of the user. Yet another example of a urine collecting bag is a urostomy collecting bag.

In examples, the collecting bag further comprises a narrowed, elongated discharge portion having a re-closable discharge opening.

The narrowed, elongated discharge portion is typically used on drainable bags such as those provided for ileostomists or on urine bags to assist the user in emptying the bag. The re-closable discharge opening may comprise sealing or safety closure means. The discharge opening may be foldable and thus be able to be folded and kept hidden and secured, typically in a pocket of the comfort layer. The collecting bag of the invention may therefore comprise a zone or areas where the comfort layer is not welded to the barrier film both to facilitate the application of the narrowed, elongated discharge portion and/or to provide a pocket for securing and hiding a folded discharge portion.

In examples, the barrier film is impermeable to water, vapour and/or gas. By impermeable is to be understood that the barrier film is able to confine the human body waste in the volume of the collecting bag at least for a pre-defined time period. Particularly with regard to gas, including foul smelling odours, it is important that the barrier film material is able to withstand the penetration thereof, at least for an acceptable wear-time of the product.

In examples, the barrier film is a laminate of different layers.

Typically, the different layers of the barrier film comprise materials such as PVDC (polyvinylidene chloride), acting as the odour retaining layer and layers containing EVA's (ethylene vinyl acetates), e.g. acting as welding or strengthening layers. In addition, other polyolefin materials such as PP (polypropylene) or PE (polyethylenes) and/or tie layers (e.g. a suitable adhesive) may be included. Typically, the barrier films may comprise multiple-layer laminates. A particularly preferred barrier film is a five-layer laminate structure of the sequence EVA-tie layer-PVDC-tie layer-EVA. Such 5-layer barrier film laminates may be available under trade names such as SaranEX 630G from Dow Europe or Nexcel MF513 from SealedAir.

The melting point of the textile material according to the invention may be in an interval ranging from 200° C.-280° C.

The melting point of the outer layers intended for melting (most often EVA-based or containing) of the barrier film material is lower, or significantly lower, than the melting point of the textile material. Typically, the outer layer(s) of the barrier film has a melting point in the range of 70° C.-120° C., depending somewhat on the materials used and particularly at least on the specific content of EVA, whereas the core or odour retaining layer (most often PVDC) has its melting point in a range from 185° C.-220° C.

In examples, the barrier film is covered by the comfort layer such that the barrier film and the comfort layer are substantially parallel. Thereby, the collecting bag is discrete and has a good effect against the build-up of a moist environment on the skin surface.

In examples, less than 75% of the fibre filaments of a thread of the textile material are embedded in the barrier film material, such as less than 50% or such as less than 25% of the fibre filaments. Thereby, the visual and tactile characteristics of the textile material in the zones of attachment may be controlled to be the same or substantially the same as the textile material outside the zones of attachment. The portion or "amount" of embedded fibre filaments may be controlled e.g. in relation to the type and quality of the textile material chosen.

A comparison between the different surface areas of the textile material may be based on physical criteria selected between several options such as degree of light reflection and/or tendency to pilling or snagging under equal conditions for the test specimens. However, a comparison may also be based on subjective criteria evaluated, e.g., by a group of test persons, e.g. criteria such as visual appeal and softness to the skin on, e.g., a 1-5 step scale.

In embodiments, the textile material is a knitted material. The knitted material may be a circle knit or a warp knit.

In preferred embodiments, the textile material is a woven material.

Both types of textiles have been found to be particularly suitable for the textile comfort layer at least because they receive and bond well with the melted material of the barrier film.

When describing woven textile materials, referrence is often made to the terms warp and weft directions: the prior term is equal to the machine direction, i.e. the primary direction of the threads in the production machinery (weave), whereas the latter, weft, is equal to the cross direction in relation to the machinery.

In embodiments, the textile is made of synthetic fibres.

Textiles made of synthetic fibres may be designed to meet particular specifications such as strength and are more cost efficient in regard to uses in mass production than natural fibres. However, natural fibre textiles such as cotton or silk materials could also be used for the comfort layer of the collecting bag.

In embodiments, where the synthetic fibre textile material is a plain 1:1 weave, the weight of the textile material per unit area (according to DS/EN 12127:1998) is in the range of 40-100 $g/m^2$, such as 60 $g/m^2$. Furthermore, the yarn number (according to DS/EN ISO 2060:1997 or ISO7211/5:1984) is in the range of 50-120 dtex (weight in grams of 10.000 meters of fibre), such as 60-90 dtex, such as 70-80 dtex. Even further, the thread density, or the number of threads per unit length (according to DS/EN 1049-2:1994), is in the range of 30-50 threads/cm in both warp and weft directions.

The above-mentioned parameters are particularly suitable with polyester materials. Thus, in embodiments said synthetic fibres are polyester fibres.

Polyester fibre based textiles have proven to be a particularly good choice for the comfort layer according to the invention. This is because polyester materials have physical characteristics such as melting point, feel and appearance that fit well with the visual, tactile and production incurred requirements of the collecting bag of the invention.

In woven textile material embodiments, the number of filaments per thread is in the range of 30-150 filaments/thread. In other words, each individual thread comprises between 30-150 individual fibre filaments.

If the woven textile material has a great number of threads per cm, it will be understood that the surface of the material is more compact, i.e. the interval or space between two neighbouring threads is reduced. If, on the other hand, the material has fewer threads per cm, the surface structure is more open or porous, i.e. the space between neighbouring threads is bigger, the textile material's bond with the melted barrier film material is facilitated because the barrier film material is allowed to flow into the spaces between the fibre filaments of the threads of the textile and bond to a much larger resulting surface.

In embodiments, the thickness of the textile material is in the range of 100-1000 µm, such as 150-200 µm.

This range of thickness is particularly well suited for the textile comfort layer because it provides a good balance between user comfort, due to light weight, discretion i.e. not being transparent, and processability during manufacture.

In embodiments, the thickness of the barrier film is in the range of 60-300 µm, such as 70-100 µm.

This range of thickness is particularly well suited for the barrier film because it provides a good balance between odour retention capability, processability during manufacture (handling in the process chain), discretion as it is not too rigid and heat lamination characteristics (able to handle the heat).

In one particular embodiment wherein the textile material is a plain 1:1 weave synthetic fibre material, the material has a weight per unit area of approx. 60 g/m$^2$, a yarn number of approx. 80 dtex in both warp and weft directions and a thread density of 42-46 threads/cm in the warp direction and 34-36 threads/cm in the weft directions.

In another aspect, the invention relates to a method for manufacturing a collecting bag for human body wastes comprising the steps of:

providing a barrier film material of the collecting bag,
providing a textile comfort layer material on said barrier film,
applying heat to the materials by a welding process at a specified process pressure and at a temperature that melts the barrier film material, but not the textile material, so that fibre filaments of said textile comfort layer and said melted barrier film material attaches to each other.

As the textile material has a higher melting point than the barrier film, the barrier film material (outer layer) will start melting at a relatively low temperature compared to the melting point temperature of the textile material while the textile does therefore not melt and upholds and remains in its interlaced structure. This also means that the structure of the textile is maintained once the materials have cooled off. In other words, when heat is applied to weld the textile to the barrier film material, the textile does not melt, but the barrier film material melts by the heat applied.

In specific embodiments of the method, the specified process pressure is controlled such that the fibre filaments of said textile material are at least partially embedded in the barrier film material.

By controlling the process pressure to a specified level, the melted barrier film material may at least partially flow into the interlaced fibre filament structure of the threads of the textile material. By "at least partially" should be understood that each fibre filament may be wholly or only partly embedded in the melted barrier film material. Thereby a physical anchorage between the two layers without destroying the structure of the textile material is created, and the textile and the barrier film materials are attached to each other, while maintaining the strength of the textile material in the resulting construction. As each thread of the textile material comprises a number of individual fibre filaments, a large resulting surface is provided for the engagement with the melted barrier film material.

In other embodiments of the method, the textile material being provided is a textile material that is chosen from the materials introduced under the description of the first aspect. The welding process may in principle be any kind of suitable welding process as known in the art that can provide the desired process temperature including welding with, e.g., a laser electrode.

In certain production set-ups, it may be beneficial to provide the comfort layer and barrier film material on top of/below and parallel to each other. This also allows for the inclusion of more than one barrier film blank so that a desired number of barrier film blanks and the comfort layer may be laminated together in the same process step. Additionally, it may also be possible to provide a second textile comfort layer in the lamination process. In the production of a collecting bag, this may provide a production set-up wherein, e.g., two barrier film blanks and a comfort layer provided on each barrier layer's outer surface may be welded into a collecting bag in a single welding step. Such process may also involve more than one source of heat for the welding, such as the provision of a laser electrode on each outer surface of the comfort layer.

Figure 1:
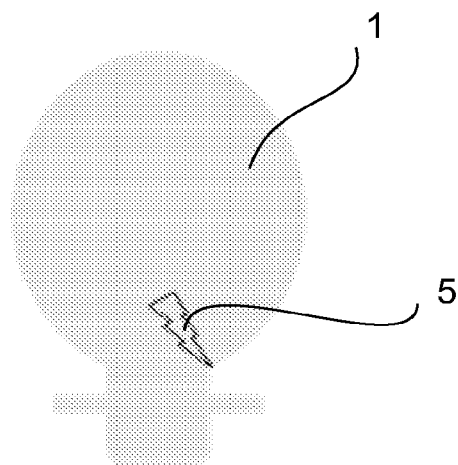
FIG. 1 is a schematic view of the outline of a drainable collecting bag of the type having a foldable outlet and indicating an area of the bag often exposed to failure, e.g. notches, caused by external forces.

It is noted that the figures, and particularly the individual elements of the figures, are not necessarily to scale, neither individually nor in relation to each other, but are basically intended to illustrate principles of the invention.

DETAILED DESCRIPTION OF THE DRAWING

FIG. 1 shows the outline of a drainable collecting bag 1 of the type having a foldable outlet and indicating an area 5 of the bag often exposed to failure caused by external forces. The area 5 is particularly exposed to such forces, most often excessive tearing, due to a number of factors, such as the fact that a user typically has to unfold the outlet several times every day to empty collected waste into a toilet bowl, and subsequently clean the outlet and fold it back into its closed or folded position. Moreover, the foldable outlet's position as an extremity of the collecting bag inevitably increases the risk that the outlet may be unintentionally pulled or get entangled with e.g. the clothes of a user, when the outlet is its unfolded position. By providing a textile comfort layer according to the present invention the risk of failure caused by such external forces is significantly reduced or eliminated.

Figure 2A:
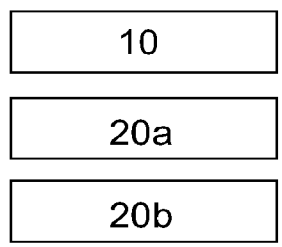
FIGS. 2a and 2b schematically illustrate the process of heat welding a comfort layer based on a non-woven material to a barrier film material as in the prior art.

FIG. 2a shows a schematic illustration of the relevant materials of a collecting bag according to the prior art in the production step prior to the welding process. Two separate layers of barrier film material 20a and 20b are provided next to each other and a single layer of a non-woven based comfort layer material 10 is provided on top of the layer 20a.

Figure 2B:
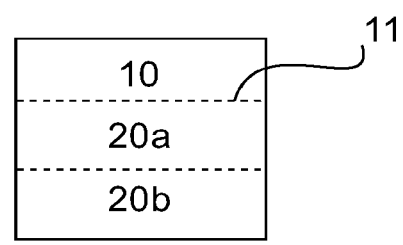

FIG. 2b schematically shows the same materials as in FIG. 2a after the welding process step. The materials 10, 20a, 20b have been bonded together by the heat applied by the welding process. The heat may be applied from one single side of the laminate construction, e.g. from the side of the comfort layer 10, or from both sides of the laminate, e.g. both from the side of the comfort layer 10 and from the side of the barrier film layer 20b. The figure illustrates how all three layers have been bonded together by melting the material of the layers into a coherent mass, the dotted line 11 representing that the engaging surfaces of the layers are no longer individually distinct. The heat provided by the welding process has melted the barrier film material 20a and 20b, but has also melted the (random) fibre structure of the non-woven material 10 whereby the welding zone hardens when it cools off and thus has no or only very little resistance towards external forces left, and is particularly prone to the creation of notches.

Figure 3A:
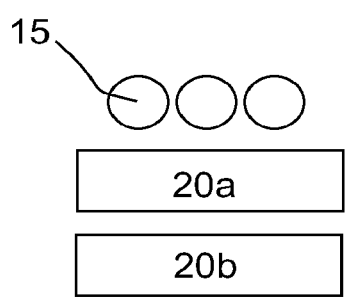
FIGS. 3a and 3b schematically illustrate the process of heat welding a comfort layer based on a textile material to a barrier film material according to the invention.

FIG. 3a is similar to FIG. 2a, only here the material of the comfort layer is no longer non-woven based, but instead a textile comfort layer according to the invention. The textile is schematically represented by three circles 15 intended to illustrate individual threads of the textile comfort layer. In practice, of course, each individual thread comprises a higher number of fibre filaments (not shown) per thread but for the sake of simplicity, the principle of the invention is shown only by way of threads and in the figure limited to three threads. Any interlaced threads of the cross-direction of the textile are also not shown in the figure.

Figure 3B:
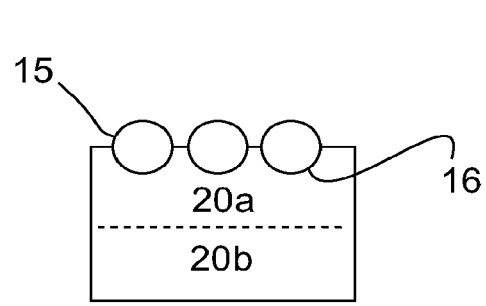

FIG. 3b is similar to FIG. 2b, but schematically illustrates how the threads 15, each comprising a number of individual fibre filaments of the textile comfort layer, are at least partly physically anchored (illustrated by example at position 16) in the melted barrier film material 20a and 20b, as the melted barrier film material flows into the structure of the threads in the textile comfort layer material without melting the fibre structure of the threads. The threads 15 of the textile material are not melted, as the textile material has a higher melting point than that of the barrier film. In reality, the melted barrier film material will flow in between the individual fibre filaments of each thread. Thus, the resulting surface of attachment between the fibre filaments and the barrier film material is significant and thereby the textile comfort layer 15 and the barrier film materials 20a, 20b are laminated to each other such that the peel strength between the barrier film material and the comfort layer is on par with that between a barrier film material and a non-woven based comfort layer, while achieving an improved resistance against external forces, such as tear forces resulting in the creation of notches.

Figure 4:
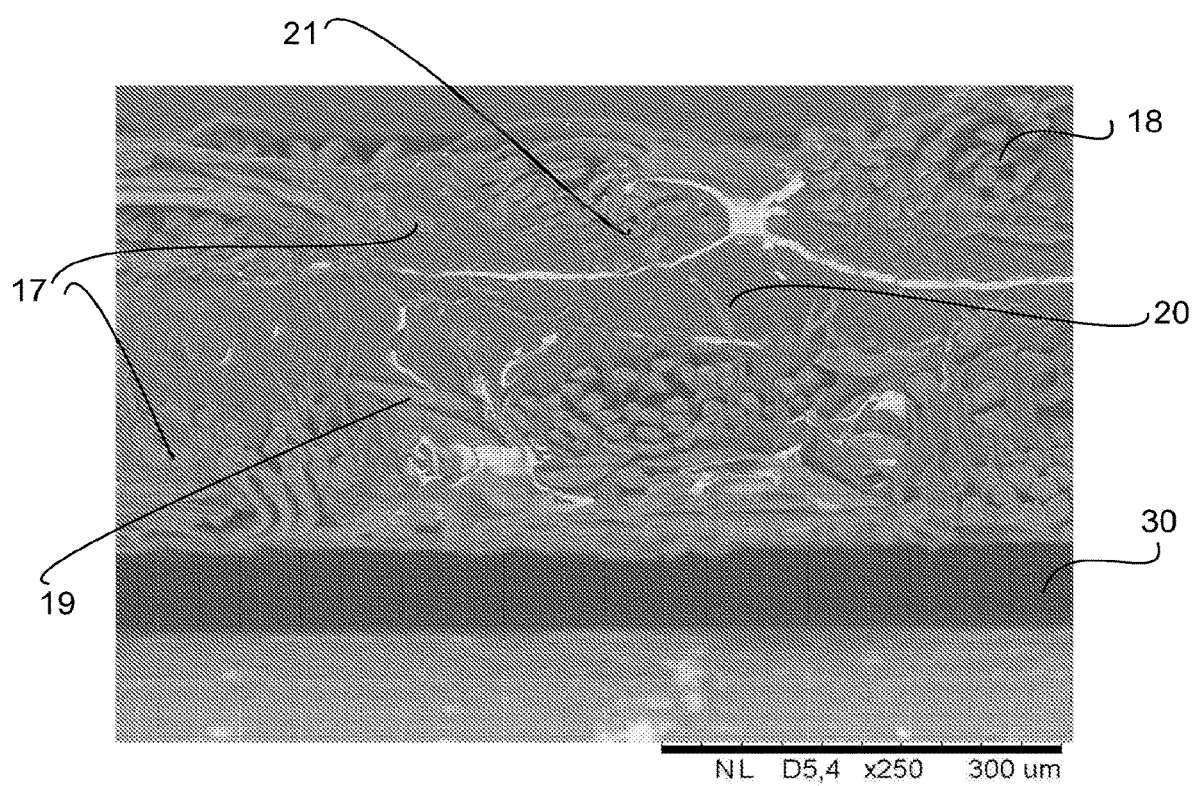
FIG. 4 is a print-out photo from a Scanning Electron Microscope showing, in cross-section, a 250-times magnification of a laminated textile comfort layer and barrier film in the welding zone of a sample collecting bag according to the invention.

FIG. 4 is a print-out photo of a 250-times magnification of the laminated textile comfort layer and barrier film in the welding zone of a sample collecting bag according to the invention. The photo shows how the schematically illustrated (FIG. 3b) principles of the invention are implemented in practice. The figure shows how some of the individual fibre filaments 17 of the threads 15 (FIG. 3b) of the textile comfort layer have been physically anchored in the melted barrier film mass 20, and also shows that not all of the fibre filaments 18 are embedded. The number of individual threads, and thus also the number of fibre filaments, is much higher than in the schematic FIG. 3a. Also, fibre filaments 19 of the interlaced threads of the cross-direction can be observed. Some fibre filaments 17 are completely embedded in the melted material 20, whereas others are only partly 21 or not at all 18 embedded in the melted material. Thus, the melted barrier film material has flowed into the space or spaces between the individual fibre filaments of the threads and the resulting surface of attachment between the fibre filaments and the barrier film material becomes significant. Thereby, the textile comfort layer 15 and the barrier film material 20a, 20b are laminated to each other such that the peel strength between the barrier film material and the comfort layer is surprisingly high.

Furthermore, still referring to FIG. 4, the fact that some filaments 18 are free from contact with the melted material 20 provides another advantage of the present invention in that a much less visible and indeed softer welding zone or area is achieved compared to collecting bags with non-woven comfort layers. In fact, the provision of the free (not melt-embedded) filaments of the textile comfort layer in practice means that, to the naked eye at least, there is no visible difference between the surface characteristics of the comfort layer in the welding zone and anywhere else on the surface of the comfort layer. The tactile feel and/or characteristics of the attachment or welding zone of a collecting bag according to the invention is also softer and less rigid than in the case of a non-woven comfort layer and is the same, or at least experienced the same by an individual, as anywhere else on the surface of the comfort layer.

The layers outside the surfaces of the textile comfort layer in FIG. 4, e.g. dark layer 30, are parts of a tool holding the sample in place during the test. It should be noted that for the test preparation, the sample of FIG. 4 was put into liquid nitrogen before cutting the cross-section out of sample, as cutting the sample at room temperature causes the textile and the barrier film material to be "mashed" into each other.

EXPERIMENTAL PART

Peel Strength between Comfort Layer and Barrier Film

The peel strength between a comfort layer and the barrier film material of a collecting bag was measured to show that for a textile based comfort layer according to the invention said peel strength is on par with that of a collecting bag having a traditional non-woven comfort layer attached to the barrier film.

Test samples included test specimens having a non-woven comfort layer attached to a SaranEX 630G barrier film material from Dow Europe and test specimens having a textile material comfort layer (approx. parameters: weight 71 g/m$^2$, yarn number 100 dtex (warp) and 94 dtex (weft) & thread density 40 threads/cm (warp) and 32 threads/cm (weft)) attached to a Nexcel MF513 barrier film material from SealedAir.

The peel strength test may be carried out either on a texture analyser, e.g. model L500X-8945 from Lloyd or model 5543 from Instron using a 50N load cell and under normal room conditions. Table 1 below shows results obtained with the texture analyser model from Instron. The tensile strength speed (or peel speed) was set to 200 mm/min.

Test procedure includes cutting a sample of the bag (test specimen) perpendicular to the attachment zone or welding 12.5 mm wide on a length of 10 cm. The holding fixtures (or jaws) holding the sample are fixed to the texture analyser, and the sample is set parallel to the pull direction. Further directions to the test can be found below for the notch sensitivity example.

Table 1 shows average measured values in [N/12.5 mm width].

TABLE 1

| Comfort layer/Barrier film | Non-woven | Textile |
|---|---|---|
| SaranEX 630G | 8.189 | |
| Nexcel MF513 | | 7.898 |

Accordingly, the peel strength using a textile based comfort layer according to the invention is found to be on par with the peel strength, when using a non-woven comfort layer.

Notch Sensitivity—External Forces Resistance

In order to show that a collecting bag for human body wastes having a comfort layer based on a textile material has an increased security against failure caused by external forces, a number of test samples were submitted to a tensile strength test, i.e. a test where the samples were torn. The tensile stress at maximum load was measured.

Test samples included 10 test specimens having a non-woven comfort layer (polypropylene spun bond, 30 g/m$^2$) and 10 test specimens having a textile comfort layer according to the invention. In each group of 10 test specimens, 5 specimens were laminated on to a SaranEX 630G barrier film material from Dow Europe and 5 specimens were laminated on to a Nexcel MF513 barrier film material from SealedAir. All test specimens included a single layer of the barrier film material and a single layer of textile material only.

The tensile stress test was carried out on a texture analyser model 5543 from Instron using a 50 N load cell, in an air-conditioned laboratory at a constant temperature of 23° C. and at constant 50% RH.

The test specimens were submitted to the tensile stress test by applying the tearing force in a position corresponding to failure area 5 on the collecting bag outlined in FIG. 1. Each test specimen was mounted in the texture analyser in such a way that the part of the sample adjacent to the left of the tearing force application position was received in a first holding jaw of the texture analyser, and the part adjacent to the right of said position was received in a second holding jaw of the texture analyser. The first holding jaw was connected to an actuator capable of providing a force in a lateral upward direction, whereas the second holding jaw was connected to another actuator providing a force in a lateral downward direction. Load cells were mounted on the holding jaws to measure the applied force at least at the time of failure. Test results are shown in the below tables 2 and 3. Table 2 shows the results of the test for the combination of the non-woven comfort layer mentioned above and the two different barrier film materials from Dow and SealedAir, also described above, respectively. Table 3 shows the results of the test for the combination of a textile material according to the invention and the respective barrier film materials mentioned.

TABLE 2

| No. | Specimen | Tensile stress at max load [MPa] |
|---|---|---|
| 1 | Non-woven + SealedAir | 16.426 |
| 2 | Non-woven + SealedAir | 16.310 |
| 3 | Non-woven + SealedAir | 16.657 |
| 4 | Non-woven + SealedAir | 17.786 |
| 5 | Non-woven + SealedAir | 16.611 |
| 6 | Non-woven + Dow | 10.354 |
| 7 | Non-woven + Dow | 7.791 |
| 8 | Non-woven + Dow | 12.145 |
| 9 | Non-woven + Dow | 11.190 |
| 10 | Non-woven + Dow | 10.493 |
| Mean | Non-woven | 13.566 |

TABLE 3

| No. | Specimen | Tensile stress at max load [MPa] |
|---|---|---|
| 1 | Textile + SealedAir | 31.015 |
| 2 | Textile + SealedAir | 30.696 |
| 3 | Textile + SealedAir | 29.172 |
| 4 | Textile + SealedAir | 29.256 |
| 5 | Textile + SealedAir | 34.941 |
| 6 | Textile + Dow | 29.172 |
| 7 | Textile + Dow | 26.320 |
| 8 | Textile + Dow | 25.354 |
| 9 | Textile + Dow | 32.432 |
| 10 | Textile + Dow | 27.635 |
| Mean | Textile | 29.599 |

As it can be clearly seen from the results of the performed tensile stress tests, a collecting bag having a textile comfort layer according to the invention has a significantly higher (more than a factor 2) resistance against failure caused by external forces. Particularly, the test results show that a collecting bag with a textile comfort layer is much less prone to failures caused by tear forces and e.g. the risk of creation of notches in the collecting bag is significantly reduced.

In conclusion, it has been shown that a collecting bag having a textile comfort layer according to the present invention has on par peel strength characteristics, but a significantly higher resistance to external forces when compared with traditional non-woven material based comfort layers. Also, the collecting bag of the invention is less dependent on the strength of the barrier film itself to resist external forces due to the use of the textile material.

Furthermore, the present invention provides a collecting bag for human body waste having improved visual and tactile characteristics in the attachment zone(s) between the barrier film material and the comfort layer as supported by the SEM photo of FIG. 4, and further an increased resistance to common wear issues such as snagging and pilling.

The invention claimed is:

1. A bag for collecting human body effluents comprising two opposing layers of a barrier film material sealingly joined to each other along a portion of an outer periphery of the opposing layers of the barrier film material, an external surface of at least one of the barrier film material layers covered by a comfort layer, wherein the comfort layer is a textile material having a number of threads, each of the threads comprising a plurality of fiber filaments, wherein the textile material is one of a woven textile material and a knitted textile material that is attached to the barrier film material in an attachment zone along the portion of the outer periphery of the opposing layers of the barrier film material, and wherein the threads of the textile material have a higher melting point than that of the barrier film material in the attachment zone.

2. The collecting bag according to claim 1, wherein less than an entirety of the fiber filaments of the textile material in the attachment zone are embedded in the barrier film material.

3. The collecting bag according to claim 1, wherein a peel strength between the comfort layer and the barrier film layer is above 5 N/12.5 mm width in the attachment zone.

4. The collecting bag according to claim 1, wherein the attachment zone is formed by the barrier film material being configured to flow into spaces between the fiber filaments of the textile material in response to heat being applied, wherein the textile material is a woven textile material and wherein each individual thread comprises between 30-150 individual fibers.

5. The collecting bag according to claim 1, wherein any fiber filaments in the attachment zone that are not embedded in the barrier film layer material provide a first portion of an external surface of the comfort layer having visual or tactile characteristics identical to visual or tactile characteristics in a second portion of the external surface of the comfort layer, the second portion located outside the attachment zone.

6. The collecting bag according to claim 1, wherein the textile material is a knitted material.

7. The collecting bag according to claim 1, wherein the textile material is a woven material.

8. The collecting bag according to claim 1, wherein a weight of the textile material is in the range of 40-100 g/m2.

9. The collecting bag according to claim 1, wherein a thread density of the textile material is in the range of 30-50 threads/cm.

10. The collecting bag according to claim 1, wherein a number of filaments per thread is in the range of 30-150 filaments/thread.

11. The collecting bag according to claim 1, wherein a thickness of the textile material is in the range of 100-1000 µm.

12. The collecting bag according to claim 1, wherein a thickness of the barrier film is in the range of 60-300 µm.

13. The collecting bag according to claim 1, wherein the textile material has an increased wear strength compared to a nonwoven comfort layer as measured by resistance to pilling evaluated according to test standard DS/EN ISO 12945-2:2000.

14. The collecting bag according to claim 1, wherein the textile material has improved resistance to pilling after washing as compared to a nonwoven comfort layer.

15. The collecting bag according to claim 1, wherein the textile material has an increased wear strength compared to a nonwoven comfort layer as measured by resistance to snagging evaluated according to test standard ASTM D3939-11.

16. An ostomy device comprising:
an adhesive base plate configured to be attached to a peristomal skin surface of a user, the adhesive base plate having a through-going hole defined around a first central axis of the through-going hole; and
a bag adapted for collecting stomal effluents, the bag comprising:
first and second barrier film material layers defining a joint outer periphery and connected to each other along a portion of the joint outer periphery, the first barrier film material layer including an inlet opening defined around a second central axis of the inlet opening aligned with the first central axis of the through-going hole of the base plate; and
a textile material layer covering an external surface of at least one of the first and second barrier film material layers, the textile material layer having a number of threads each comprising a plurality of fiber filaments;
wherein, the textile material layer is welded to the at least one of the first and second barrier film material layers in an attachment zone along the joint outer periphery, and
wherein the threads of the textile material have a higher melting point than that of the barrier film material in the attachment zone.

17. A method for manufacturing a collecting bag for human body wastes comprising the steps of:
providing two opposing layers of a barrier film material,
providing a textile comfort layer having a higher melting point than the barrier film material,
covering an exterior portion of at least one of the two opposing layers of the barrier film material with the textile comfort layer,
applying heat and pressure by a welding process and melting the barrier film material, but not the textile comfort layer, so that some, but not all, fibre filaments of threads of said textile comfort layer are embedded in melted barrier film material at an outer periphery of the two opposing layers of the barrier film material, and thus attaching the textile comfort layer to the barrier film material.

18. The method of claim 17, comprising covering the exterior portion of one of the two opposing layers of the barrier film material with a first textile comfort layer and covering the exterior portion of a second of the two opposing layers of the barrier film material with a second textile comfort layer.

19. An ostomy bag comprising:
a first barrier film sealed to a second barrier film along a portion of a melted outer periphery of the first barrier film and the second barrier film to form a pouch;
a first comfort layer covering a portion of the first barrier film;
wherein the first comfort layer is a textile material having a number of threads, and the textile material is one of a woven textile material and a knitted textile material;
wherein the threads of the textile material have a higher melting point than a melting point of the first barrier film material such that the threads of the textile material of the first comfort layer are embedded into the melted outer periphery of the first barrier film and the second barrier film.

* * * * *

UNITED STATES PATENT AND TRADEMARK OFFICE
CERTIFICATE OF CORRECTION

PATENT NO. : 10,973,677 B2  
APPLICATION NO. : 16/005708  
DATED : April 13, 2021  
INVENTOR(S) : Markus Freiding Page 1 of 1

It is certified that error appears in the above-identified patent and that said Letters Patent is hereby corrected as shown below:

On the Title Page

In Item (74), under "Attorney, Agent, or Firm", in Column 2, Lines 1-2, delete "Coloplast Corp.; Nick Baumann" and insert -- Coloplast Corp., Coloplast A/S; Nick Baumann --, therefor.

In the Specification

In Column 8, Line 28, delete "invention, and" and insert -- invention; and --, therefor.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*